United States Patent
Woirgard et al.

(10) Patent No.: US 7,685,868 B2
(45) Date of Patent: Mar. 30, 2010

(54) MEASURING HEAD FOR NANOINDENTATION INSTRUMENT AND MEASURING METHOD USING SAME

(75) Inventors: Jacques Woirgard, La Grimaudiére (FR); Bertand Bellaton, Neuchâtel (CH); Richard Consiglio, Neuchâtel (CH)

(73) Assignee: CSM Instruments SA, Peseux (CH)

( * ) Notice: Subject to any disclaimer, the term of this patent is extended or adjusted under 35 U.S.C. 154(b) by 371 days.

(21) Appl. No.: 11/721,997
(22) PCT Filed: Nov. 16, 2005
(86) PCT No.: PCT/EP2005/056026

§ 371 (c)(1),
(2), (4) Date: Jun. 18, 2007

(87) PCT Pub. No.: WO2006/069847

PCT Pub. Date: Jul. 6, 2006

(65) Prior Publication Data
US 2009/0260427 A1    Oct. 22, 2009

(30) Foreign Application Priority Data
Dec. 23, 2004    (EP)    ................... 04405798

(51) Int. Cl.
G01N 3/48    (2006.01)
(52) U.S. Cl. .......................................... 73/81
(58) Field of Classification Search ............ 73/85, 73/81, 83
See application file for complete search history.

(56) References Cited

U.S. PATENT DOCUMENTS 4,635,471 A    1/1987    Rogers et al.
4,820,051 A    4/1989    Yanagisawa et al.
4,852,397 A    8/1989    Haggag
5,027,650 A    7/1991    Oblas et al.
5,553,486 A    9/1996    Bonin
6,247,356 B1    6/2001    Merck, Jr. et al.
6,718,820 B2*    4/2004    Kwon et al. ................... 73/81

OTHER PUBLICATIONS

XP000723539 Simamoto A et al: "Development of a Depth Controlling Nanoindentation Tester wiith Subnanometer Depth and Submicro-Newton Load Resolutions" Review of Scientific Instruments, American Institute of Physics. New York, US, vol. 68, No. 9, Sep. 1997, pp. 3494-3503, ISSN: 0034-6748 Abstract p. 3494-p. 3495; figure 1, Sep. 1997.
International Search Report PCT/EP2005/056026 related to subject application, Mar. 2006.
International Search Report in French PCT/EP2005/056026 related to subject application, Nov. 2005.
European Search Report related to subject application, May 2005.

* cited by examiner

Primary Examiner—Hezron Williams
Assistant Examiner—Nathaniel Kolb
(74) Attorney, Agent, or Firm—Townsend M. Belser, Jr.; Nexsen Pruet, LLC

(57) ABSTRACT

A measuring head for a nano-indentation instrument capable of positioning a sample relatively to the measuring head, which includes a measuring axis, a reference axis and a component for detecting a depth of penetration of an indentor into the sample. The measuring and reference axes are attached to a frame for connection to the instrument. The measuring axis incorporates an actuator and includes the indentor, the reference axis incorporates an actuator and includes a reference tip, and the measuring and reference axes each have a component for detecting a force applied by its actuator. Penetration depth is detected by measuring a displacement of the indentor relatively to the reference tip.

20 Claims, 3 Drawing Sheets

MEASURING HEAD FOR NANOINDENTATION INSTRUMENT AND MEASURING METHOD USING SAME

BACKGROUND OF THE INVENTION

1) Field of Invention

The present invention generally relates to nano-indentation measuring instruments and more particularly to a measuring head for such an instrument as well as to its method of use, said head using active referencing of the surface of the sample to be measured.

2) Description of Related Art

The measuring method by instrumented indentation (Depth-Sensing Indentation or DSI) is one of the most used methods for determining certain mechanical properties of materials, such as for example the elastic modulus and hardness. This method consists of applying an increasing and subsequently a decreasing force on a sample via a tip or indentor, with a determined shape in order to investigate and to measure, continuously and simultaneously, the values of the load, of the load alleviation, respectively, applied onto the sample on the one hand, and the penetration depth of the indentor on the other hand. The involved forces may be extremely weak, typically of the order of a few micro-Newtons (μN), and the displacements of the indentor to be measured may be of the order of one nanometer (nm). One then speaks of nano-indentation.

A head for nano-indentation measurements should therefore be capable of applying a force on a sample via an indentor and of determining the applied force as well as the corresponding penetration of the indentor. Among the existing nano-indentation measuring instruments, the Nano Hardness Tester or NHT, may be cited, marketed by the applicant or further the instrument "Triboindenter®" of Hysitron Inc. The technology used for the measuring head of this latter instrument is moreover described in U.S. Pat. No. 5,553,486. The measuring heads of the prior art apply the desired force via an electrodynamic (electro-magnet) or electrostatic actuator and they have a displacement sensor (generally a capacitive sensor) but no force sensor. The force applied to the sample is then inferred from the force generated by the actuator, for example calculated from the current or voltage applied to the latter and from the stiffness of the spring strips supporting the indentor. This is therefore a method for indirect measurement of the applied force.

U.S. Pat. No. 4,852,397 describes a measuring instrument by nano-indentation, the measuring head of which includes an indentor, actuating means as well as detecting means of the penetration depth of the indentor in a sample by direct measurement.

The publication entitled "Development of a depth controlling nano-indentation tester with subnanometer depth and submicro-newton load resolutions", published under the names of Atsushi Shimamoto and Kohichi Tanaka, in Volume 68(9) of September 1997 of the Review of Scientific Instruments, pp. 3494-3503, discloses another example of such a measuring apparatus. The latter comprises a measuring head, including an indentor and a displacement sensor, both submitted to the action of a single actuator, as well as means for measuring the load applied by the actuator, distinct from the measuring head. The displacement sensor described in this publication is of the optical fiber type and with it, direct optical measurement of the displacement of the measuring head may be carried out.

Generally, with the cited devices of the prior art, several problems arise, such as the following:

1) Thermal drift. A standard nano-indentation measurement lasts for about one minute. During this period, any change in temperature will result in a dimensional change of the mechanical components of the measuring instrument (thermal expansion or contraction). The problem is further worsened if the instrument uses an electrodynamic actuator which itself produces heat and this depends on the generated force. For example, in the case of a system without any reference, if a path of 30 cm is considered between the tip of the indentor and the surface of the sample, via the frame of the steel instrument (thermal expansion coefficient of steel equal to $10\times10^{-6}/°$ C.), a variation of 0.1° C. during the measuring period would lead to a depth measuring error of the order of 300 nm, which is disproportioned with regard to the penetration depths which themselves are frequently less than 100 nm. Present answers for minimizing thermal variations combine the use of costly thermostated enclosures with an action consisting of measuring the drift at a given instant and of applying a correction of this drift to the totality of the nano-indentation measurement. Such answers lead to very long cycle times (waiting for thermal stabilization in the enclosure) and are based on the arbitrary assumption that the thermal drift remains constant throughout the measurement.

2) Influence of the stiffness of the frame of the instrument and of the frame-sample connection. When a force is applied on the indentor, it not only causes a penetration of the indentor into the sample but also a deformation of the sample holder/instrument assembly proportional to the compliance (which means the capability of deforming under the effect of a stress) of this assembly. This deformation leads to overestimating the penetration depth and requires subsequent correction by subtraction of the estimated value of the compliance. A solution, already used by the applicant to counter this problem, consists of having the measuring head directly rest on the sample via a reference part and next measuring the penetration depth directly between this reference and the indentor. Any parasitic movement (whether from a thermal origin or because of the compliance of the frame) will thus be greatly attenuated. One of the problems in this case, is that the totality of the weight of the measuring head rests on the sample, which poses problems on soft materials or materials exhibiting creep because, in this case, solving a problem creates new problems.

3) Independence of the force and displacement sensors. As indicated earlier, the existing nano-indentation heads are equipped with a single actuator and a single sensor (displacement sensor). The absence of an independent force sensor poses two problems. First, the force is not directly measured but is estimated, which may be a source of error, and second, several very interesting loading modes—such as an indentation with a constant deformation rate for example—cannot be applied completely because they require a control which takes into account the penetration depth and the applied force simultaneously.

SUMMARY OF THE INVENTION

The object of this invention is therefore to allow a nano-indentation measurement, free from the constraints mentioned earlier and to thereby obtain a more accurate and more reliable measurement of the elastic modulus and of the hardness at a nanoscale. This object is achieved by means of the measuring head defined in the independent claim. Particularly advantageous exemplary embodiments are defined in certain dependent claims. A measuring method using the measuring head of the invention is the object of other dependent claims.

The invention is based on the idea of using a measuring axis and a reference axis each having their own actuating means and their own means for measuring the displacement, and of measuring the applied force. The indentation measurement may therefore be conducted relatively to a reference, for which the force applied on the sample is controlled. Thus it is possible to achieve what is called active referencing of the surface of the sample to be measured, i.e., by independently controlling the reference axis, it is possible to get rid of any parasitic movement of the surface of the sample and/or of the measuring instrument itself, for example as a result of a change in temperature, of a deformation of the frame or of the frame-sample connection.

The measuring head according to the invention is further designed so as not to generate any heat and to be also as insensitive as possible to any change in room temperature. Its application does therefore not require it being placed in a thermostated enclosure.

BRIEF DESCRIPTION OF THE DRAWINGS

Other objects, features and advantages of the present invention will become apparent upon reading the following description made as a non-limiting example and with reference to the appended drawings wherein.

DETAILED DESCRIPTION OF THE INVENTION

Figure 1:
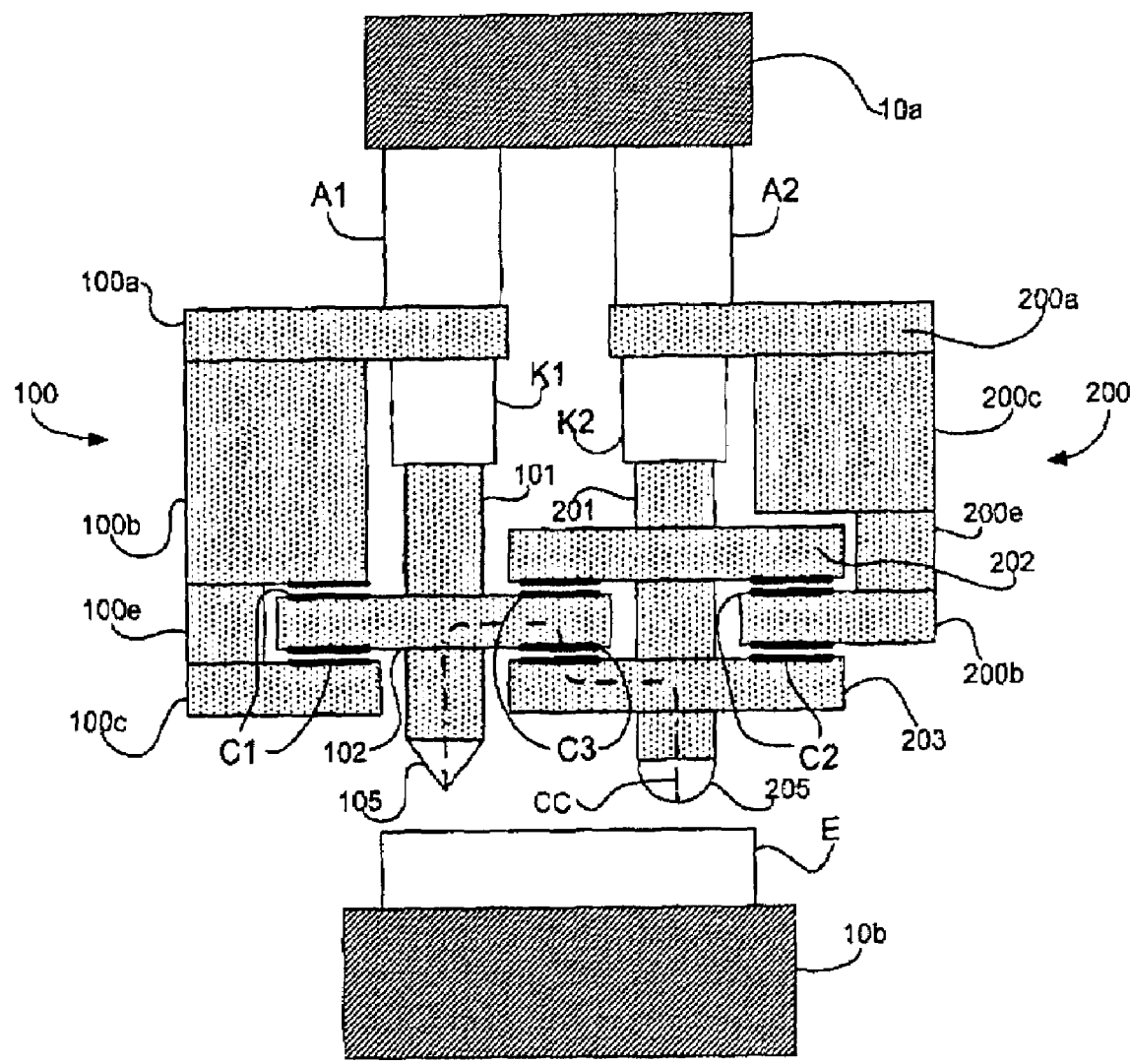
FIG. 1 shows an exemplary embodiment of the measuring head according to the invention.

An exemplary embodiment of a measuring head by nanoindentation according to the principles of the invention is schematically illustrated in FIG. 1. This measuring head has, attached to the frame 10 of the measuring instrument, two symmetrical and independent axes, one of the axes corresponding to the actual indentor and the second axis corresponding to the reference. Thus, for the axis corresponding to the indentor and called a measuring axis, an actuator A1, preferably of the piezoelectric type, attached to the frame 10a, a spring K1 and a rod 101 ending with the indentor 105, are found. The rod 101 includes a transverse component 102 which bears lower and upper electrodes, which cooperate with matching electrodes on the portions 100b and 100c of the body 100 so as to form a force sensor in the form of two capacitors C1, mounted differentially so as to measure the deformation of the spring K1. The body 100, which includes the portions 100a-100e, is attached by its portion 100a to the actuator A1 on the one hand and to the spring K1 on the other hand. For the axis corresponding to the reference and called a reference axis, an actuator A2, also attached to the frame 10a and of the piezoelectric type, a spring K2 and a rod 201 ending with a reference head 205 are found. The rod 201 includes transverse components 202 and 203 which bear electrodes on their internal face. These electrodes cooperate with the matching electrodes borne by the transverse component 102 in order to form a penetration depth sensor C3 on the one hand, and, with matching electrodes on the portion 200b of the body 200, in order to form an applied force sensor, so as to measure the deformation of the spring K2 on the other hand. As for the capacitor C1, the capacitors C2 and C3 are made up so as to each form two differentially mounted capacitors. The body 200, which includes the portions 200a-200e is attached by its portion 200a to the actuator A2 on the one hand, and to the spring K2 on the other hand. FIG. 1 further shows a sample holder 10b on which the sample E to be measured may be attached. The sample holder 10b is connected to the frame 10a of the measuring instrument by positioning means (not shown) so that the sample may be brought to the desired position (x, y and z) under the measuring head. Of course, these positioning means are known to one skilled in the art and will therefore not be described any further.

The bodies 100 and 200 should be perfectly stiff, have a mass as low as possible and also have a thermal expansion coefficient as small as possible. Ceramic glass, as marketed by Schott under the brand Zerodur®, meets the stated conditions. This material will advantageously also be used for making the rods 101 and 201, as well as the transverse components 102, 202 and 203. The material of the indentor 105 and that of the reference head will depend on the application. As a non-limiting example, the indentor may be in diamond and the reference head in steel. As indicated earlier, the actuators A1 and A2 will preferably be of the piezoelectric type in order to avoid any generation of heat. An exemplary embodiment of such actuators will be described with reference to FIG. 3a. The springs K1 and K2 should have a low weight and bulk, have good linearity and be as insensitive as possible to temperature. An exemplary embodiment of such springs will be described with reference to FIG. 3b. The electrodes, forming the sensors C1-C3, may be made by depositing a thin layer of chromium, forming an adhesion layer, on which a gold layer will then be deposited.

As for the measuring head as described above, it is further important that it meets the following conditions:
the total suspended mass should be as low as possible;
both measuring and reference axes should be as symmetrical as possible (same length and same materials used); and
the critical path or length of the measuring loop (dotted line CC from the tip of the indentor to the tip of the reference head) should be minimal, which implies that the distance between the indentor and the reference tip is also minimal.

Figure 2:
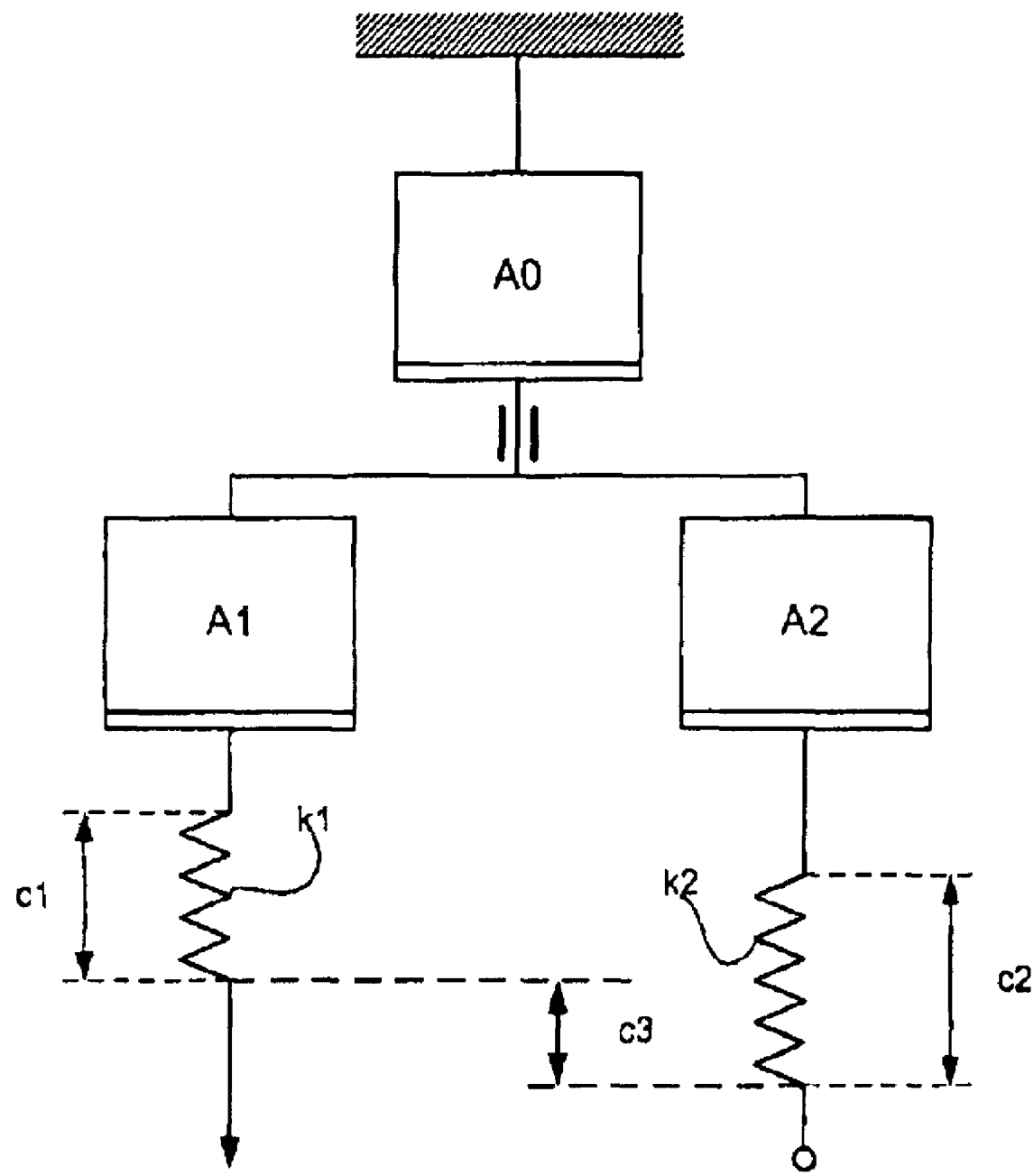
FIG. 2 is an explanatory diagram of the measuring head of FIG. 1.

The operation of the measuring head of the invention and in particular that of the sensors may be explained with the diagram of FIG. 2. Block A0 symbolizes the positioning means which bring the sample E to the intended position relatively to the measuring head. In this position, the reference head should be in contact with the sample. The force $F_N$ref applied by the latter on the sample is equal to $c_2 \cdot k_2$, where $c_2$ is the displacement of the reference rod relatively to the body 200 as measured by the sensor C2 (see FIG. 1) and $k_2$ is the constant of the spring K2. In the same way, the force $F_N$ applied by the indentor is equal to $c_1 \cdot k_1$, where $c_1$ is the displacement of the rod of the indentor relatively to the body 100, as measured by the sensor C1 and $k_1$ is the constant of the spring K1. The forces $F_N$ and $F_N$ref are of course generated by the actuators A1 and A2, respectively. Finally, $c_3$ represents the displacement between the reference rod and the rod of the indentor which is measured by the sensor C3 (see FIG. 1) and which is the penetration depth of the indentor.

Figure 3A:
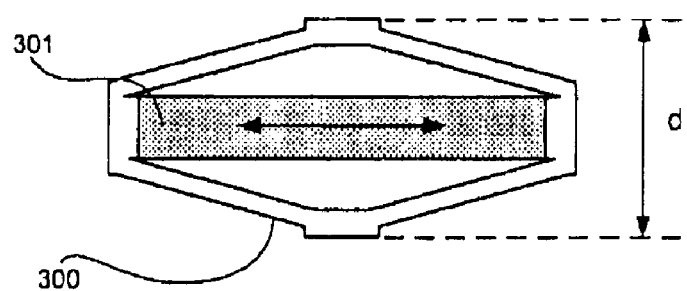
FIGS. 3a and 3b illustrate a piezoelectric actuator with amplification and a spring, respectively, as used in the measuring head of FIG. 1.

FIG. 3a shows a so-called "amplification" actuator which may be used in the measuring head according to the invention. Such an actuator is of the APA 120S type, as marketed by Cedrat Technologies, Aix, France. It is controlled by a DC voltage which may attain 150 volts and has a stroke of 100

μm. It consists of a bar 301 in piezoelectric material (to which the DC voltage is applied via suitable electrodes) and of a frame 300 with a rhombic shape and transforming a horizontal elongation of the bar into a vertical displacement of the free angles of the rhombus. The actuator is laid out in such a way that the vertical displacement is larger than the elongation of the bar, whence its name of amplification actuator. It is understood that other actuators may be used from the moment that they meet the conditions stated earlier.

Figure 3B:
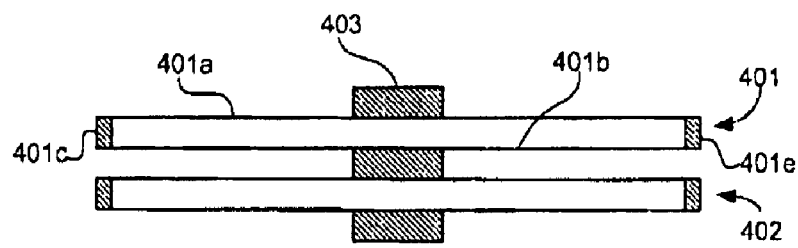

FIG. 3*b* shows a type of spring which may be used in the measuring head according to the invention. It includes several rectangular structures (such as 401 and 402), formed with two flexible strips (such as 401*a* and 401*b*) joined by stiff end components (401*c* and 401*e*). The rectangular structures are joined to each other by interfaces (403) fixed at the center of the flexible strips. Under the effect of an applied force between the external portions of these interfaces, the flexible strips deform linearly. The material advantageously used for making these springs is invar, which is an iron and nickel alloy well-known for its exceptional thermal properties. There again, the exemplary embodiment described above is non-limiting and other types of spring may also be used.

Figure 4:
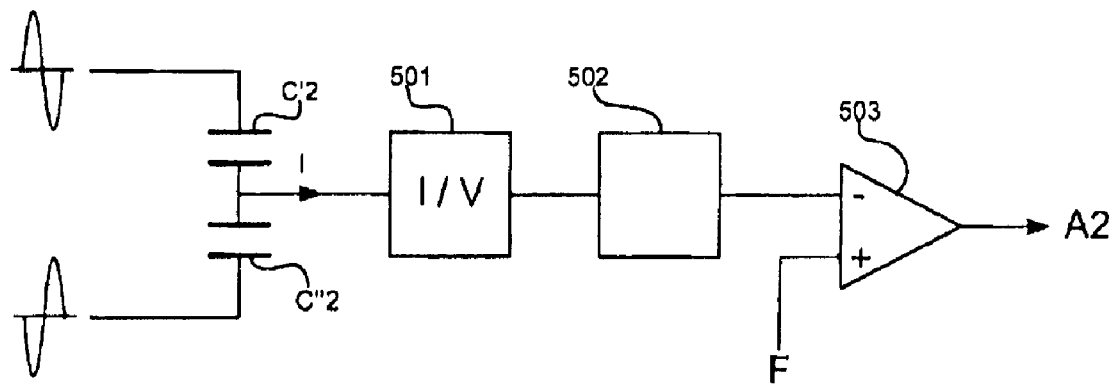
FIG. 4 shows an exemplary circuit used for servo-controlling the actuator of the reference axis of the measuring head of FIG. 1.

FIG. 4 schematically shows an exemplary circuit which may be used for controlling the actuator A2 so that the applied force by the reference head on the sample is maintained at a constant set value. The capacitors C'2 and C"2 represent the sensor C2 of FIG. 1. They are connected in series and their central plate is capable of moving (when the position of the reference head changes), thereby changing the value of the capacitors C'2 and C"2 without however changing the value of their sum which remains constant. A first sine-wave signal is applied on the external plate of C'2 and a second sine-wave signal with the same amplitude as the first but with opposite phase, is applied on the external plate of C"2. The resulting signal on the central plates of C'2 and C"2 which is a measurement of displacement of the central plate, is applied at the input of a current/voltage conversion circuit 501, the output of which, after filtering by means of the filter 502, is applied to the inverting input of a amplifier-comparator 503. The non-inverting input of the comparator 503 receives a voltage representing the value F of the force to be applied on the reference head. Thus, the circuit 503 delivers a voltage for controlling the actuator A2 which is proportional to the difference between the measured force by means of the sensor C2 and the set force F.

According to an advantageous alternative of the invention, a servo-control circuit is also provided for the servo-control of the actuator A1 of the measuring axis. However, in this case, the set force may not be constant but may change during a same measuring cycle or even from one cycle to the other.

According to another alternative of the invention, the actuator A1 of the measuring axis is controlled in such a way that the displacement of the indentor is servo-controlled to a given value.

The method for using the measuring head according to the invention includes the following steps:

the piezoelectric actuators A1 and A2 are pre-positioned so that the tip of the indentor is first slightly retracted relatively to the reference head;

next, the sample E is displaced vertically until it is brought into contact with the reference head;

the piezoelectric actuator A2 is consequently controlled so that a selected force is applied to the reference head and this during the whole measuring period;

the indentor is then, by means of the actuator A1, brought into contact with the sample E, the contact force being controlled by the force sensor (C2, K2);

starting the measuring cycle consisting of applying a given force to the indentor (a simply variable static force or variable according to a repetitive sequence, etc.) and of simultaneously measuring the penetration depth of the indentor;

retracting, at the end of the measurement or of the measuring cycles, first the indentor, and then the reference head and finally the sample.

Although the present invention was described with reference to particular exemplary embodiments, it is by no means limited to said examples and may undergo changes and/or alternatives without however departing from its scope. In particular, if in the preceding description, the stiffnesses of the springs K1 and K2 were supposed to be equal, it is also conceivable to make them different, this would, by swapping the measuring axis and the reference axis (which amounts to exchanging the indentor and the reference tip) very easily provide two different measurement ranges on the same instrument.

The invention claimed is:

1. A measuring head for a nano-indentation instrument having positioning means capable of positioning a sample relatively to said measuring head, which comprises:

a measuring axis attached to a frame intended to be connected to said instrument, incorporating first actuating means and including an indentor;

means for detecting a depth of penetration of said indentor in said sample; and, a reference axis also attached to said frame, incorporating second actuating means and including a reference tip;

wherein said measuring axis and said reference axis each comprise means for detecting a force applied by said first and second actuating means, and wherein detection of said penetration depth is performed by measuring a displacement of said indentor relatively to said reference tip.

2. The measuring head according to claim 1, wherein said measuring axis and said reference axis comprise first spring components, positioned between said first actuating means and said indentor, and second spring components positioned between said second actuating means and said reference tip, respectively, as well as sensors for a displacement of the indentor relative to said first actuating means, and from said reference tip relative to said second actuating means, respectively.

3. The measuring head according to claim 2, wherein said displacement sensors are capacitive sensors.

4. The measuring head according to claim 1, wherein said detection of said penetration depth is also performed with a capacitive sensor.

5. The measuring head according to claim 3, wherein said capacitive sensors are differential type sensors.

6. The measuring head according to claim 1, wherein said first and second actuating means are piezoelectric type actuating means.

7. The measuring head according to claim 1, wherein said measurement axis and said reference axis are identical in length and materials.

8. The measuring head according to claim 1, wherein said measurement axis and said reference axis are made in materials, respectively, with a thermal expansion coefficient below 0.5×10E-6/K.

9. The measuring head according to claim 1, wherein it comprises a servo-control circuit of said second actuating means in order to control a force applied on said sample by said reference tip.

10. The measuring head according to claim 1, wherein it comprises a servo-control circuit of said first actuating means in order to control a force applied by the indentor on the sample.

11. The measuring head according to claim 1, wherein it comprises a servo-control circuit of said first actuating means in order to control said penetration depth of said indentor.

12. The measuring head according to claim 4, wherein said capacitive sensors are differential type sensors.

13. The measuring head according to claim 2, wherein said first and second actuating means are piezoelectric type actuating means.

14. The measuring head according to claim 2, wherein said measurement axis and said reference axis are identical in length and materials.

15. The measuring head according to claim 2, wherein said measurement axis and said reference axis are made in materials, respectively, with a thermal expansion coefficient as small as possible.

16. The measuring head according to claim 2, wherein it comprises a servo-control circuit of said second actuating means in order to control a force applied on said sample by said reference tip.

17. The measuring head according to claim 2, wherein it comprises a servo-control circuit of said first actuating means in order to control a force applied by the indentor on the sample.

18. The measuring head according to claim 2, wherein it comprises a servo-control circuit of said first actuating means in order to control said penetration death of said indentor.

19. A nano-indentation measurement method employing a nano-indentation instrument having a measuring head and positioning means capable of positioning a sample relatively to said measuring head, which instrument comprises:

a measuring axis attached to a frame intended to be connected to said instrument, incorporating first actuating means and including an indentor;
  means for detecting a depth of penetration of said indentor in said sample; and,
  a reference axis also attached to said frame, incorporating second actuating means and including a reference tip;
  said measuring axis and said reference axis each comprising means for detecting a force applied by said first and second actuating means,
  and said detection of said penetration depth being performed by measuring a displacement of said indentor relatively to said reference tip, said measurement method comprising steps of:

positioning a sample to be analyzed under the measuring head,
  pre-positioning said sample as well as said first and second actuating means so that said reference tip is in contact with said sample and said indentor is slightly retracted relatively to a surface of said sample,
  controlling said second actuating means so that said reference tip applies a given force on said sample,
  controlling said first actuating means in order to bring said indentor in contact with said sample,
  carrying out a measurement by controlling said first actuating means so that said indentor applies an intended force on said sample while measuring simultaneously said penetration depth of said indentor into said sample, and
  retracting said indentor and then said reference tip and then said sample at the end of said measurement.

20. The method according to claim 19, wherein said measurement comprises a plurality of penetration cycles according to a given sequence.

* * * * *